(12) United States Patent
Mimura et al.

(10) Patent No.: US 9,080,935 B2
(45) Date of Patent: Jul. 14, 2015

(54) IMAGE ANALYSIS METHOD FOR CELL OBSERVATION, IMAGE-PROCESSING PROGRAM, AND IMAGE-PROCESSING DEVICE

(75) Inventors: Masafumi Mimura, Ageo (JP); Kei Ito, Okegawa (JP)

(73) Assignee: NIKON CORPORATION, Tokyo (JP)

( * ) Notice: Subject to any disclaimer, the term of this patent is extended or adjusted under 35 U.S.C. 154(b) by 1156 days.

(21) Appl. No.: 12/923,514

(22) Filed: Sep. 24, 2010

(65) Prior Publication Data

US 2011/0013821 A1    Jan. 20, 2011

Related U.S. Application Data

(63) Continuation of application No. PCT/JP2009/054758, filed on Mar. 12, 2009.

(30) Foreign Application Priority Data

Mar. 24, 2008 (JP) ................ 2008-075668
Mar. 24, 2008 (JP) ................ 2008-075670

(51) Int. Cl.
*G06K 9/46* (2006.01)
*G01N 15/14* (2006.01)
*G06T 7/00* (2006.01)

(52) U.S. Cl.
CPC .......... *G01N 15/1475* (2013.01); *G06T 7/0016* (2013.01); *G06T 2207/10056* (2013.01); *G06T 2207/30024* (2013.01)

(58) Field of Classification Search
CPC ............. G01N 15/1475; G06T 7/0016; G06T 2207/10056; G06T 2207/30024
USPC ........................ 382/128, 133, 131
See application file for complete search history.

(56) References Cited

U.S. PATENT DOCUMENTS 6,917,884 B2 * 7/2005 Sammak et al. ............... 702/21
8,463,015 B2 * 6/2013 O Ruanaidh et al. ......... 382/133
(Continued)

FOREIGN PATENT DOCUMENTS

| JP | 7-332930 | 12/1995 |
| JP | 3298355 | 4/2002 |
| JP | 2006-6131 | 1/2006 |

OTHER PUBLICATIONS

Jorg Grunwald, "Time-Lapse Video Microscopic Analysis of Cell Proliferation, Motility and Morphology: Applications for Cytopathology and Pharmacology," BioFeature, BioTechniques, vol. 5, No. 7, 1987, p. 680-687.

(Continued)

*Primary Examiner* — Samir Ahmed
(74) *Attorney, Agent, or Firm* — Staas & Halsey LLP

(57) ABSTRACT

An image-processing program for cell observation comprises obtaining a first image showing a plurality of cells in an observation region, the first image being captured by an imaging device, and a second image showing the observation region, the second image being captured by the imaging device a predetermined time before the first image is captured; selecting one cell as a cell of interest from the plurality of cells included in the first image; specifying cells on the periphery of the cell of interest as peripheral cells; calculating movement statistics of the peripheral cells with respect to the cell of interest on the basis of the amount of relative movement of the cell of interest and the peripheral cells in the first image and the second image; and outputting the calculated movement statistics of the peripheral cells.

28 Claims, 12 Drawing Sheets

(56) References Cited

U.S. PATENT DOCUMENTS

| | | | | |
|---|---|---|---|---|
| 2008/0279441 | A1* | 11/2008 | Matsuo et al. | 382/133 |
| 2009/0232381 | A1* | 9/2009 | Matsunaga et al. | 382/133 |
| 2010/0260406 | A1* | 10/2010 | Sammak et al. | 382/133 |
| 2012/0028288 | A1* | 2/2012 | Nitta | 435/29 |

OTHER PUBLICATIONS

Alireza S. Mahani et al., "Iterative Cooperation Between Parallel Pathways for Object and Background Motion," Biological Cybernetics, Springer-Verlag, 2006, p. 393-400.
Shiro Kanegasaki et al., "A Novel Optical Assay System for the Quantitative Measurement of Chemotaxis," Journal of Immunological Methods, 2003, p. 1-11.
Lisa Choi et al., "Description of Chemotactic Cell Migration Via Optical Flow Methods," ASME, 2000, p. 109-110.
Tetsuaki Tsuchido et al., "Application of Dynamic Image Analysis of Bacterial Cell Motion in Biotechnology," Bioscience and Industry, vol. 54, No. 4, 1996, p. 281-282.
International Search Report for PCT/JP2009/054758, mailed Jun. 9, 2009.
Extended European Search Report issued Feb. 22, 2013, in corresponding European Patent Application No. 09725736.4.
Luciana da Fontoura Costa et al., "A Framework for Cell Movement Image Analysis", 2003, pp. 1-6.
Bruce Albert et al., "Molecular Biology of the Cell", Second Edition (Japanese Translation) pp. 748-749 and pp. 1188-1190.
Bruce Albert et al., "Molecular Biology of the Cell", Nov. 10, 1993, Second Edition (Japanese Translation) pp. 748-749 and pp. 1188-1190.

* cited by examiner

FIG. 8
(1) 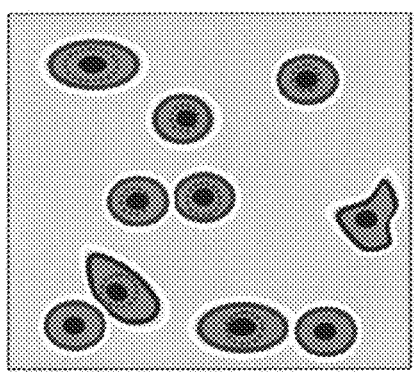 (2) 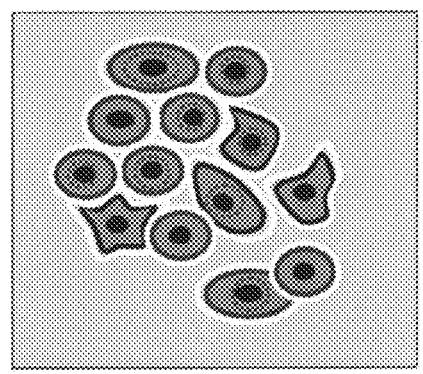

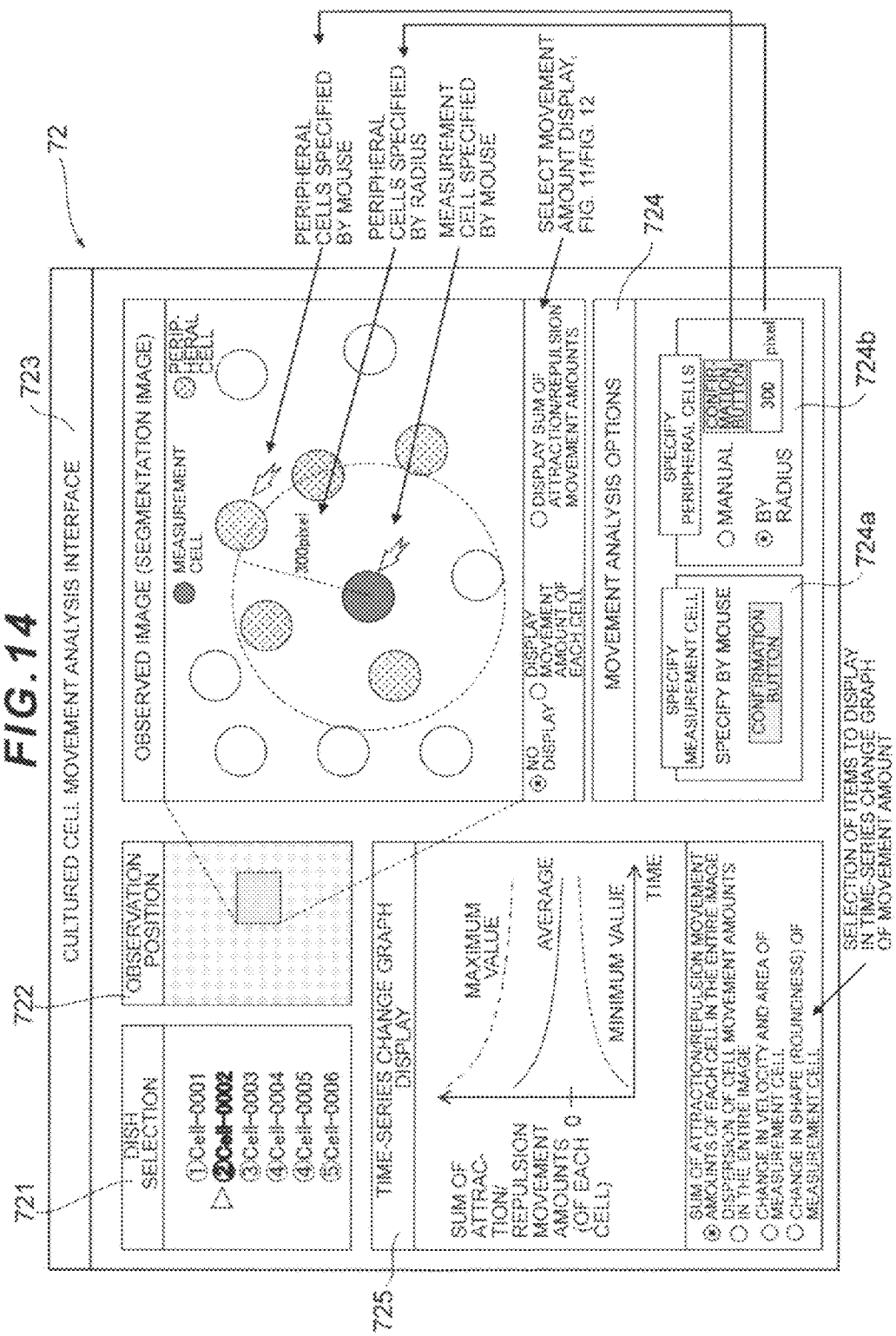

IMAGE ANALYSIS METHOD FOR CELL OBSERVATION, IMAGE-PROCESSING PROGRAM, AND IMAGE-PROCESSING DEVICE

CROSS-REFERENCE TO RELATED APPLICATIONS

This is a continuation of PCT International Application No. PCT/JP2009/054758, filed on Mar. 12, 2009, which is hereby incorporated by reference. This application also claims the benefit of Japanese Patent Application No. 2008-075668 and Japanese Patent Application No. 2008-075670, filed in Japan on Mar. 24, 2008, which are hereby incorporated by reference.

TECHNICAL FIELD

The present invention relates to an image processing method for cell observation, for analyzing the movement state of a cell from images obtained by observing the cell at predetermined times.

TECHNICAL BACKGROUND

Cell division is a fundamental piece of information about cell movement. Cell division and the formation of scaffolding are typically thought to be related, and a more normal growth rate can be maintained by a group of cells gathered together than by a cell that exists in isolation. Depending on the cell, a growth factor such as PDGF (platelet-derived growth factor) is sometimes secreted to control the growth of the other cells in the group (e.g., see Non-patent Document 1). Cell growth is thus controlled by social interaction.

Conventionally, states in which cells are grown or inhibited as described above are determined by using a microscope to observe a cell at regular time intervals, capturing a plurality of microscopically observed images, and assessing these captured images. For example, binary observation is used to determine that a state in which cells have bound together into a colony upon being observed indicates a cell-behavior-induced change from individual cells to a colony of cells.

Non-patent Document 1: Albert, Bruce et al., K. Nakamura and K. Matsubara tr., Molecular Biology of the Cell, $2^{nd}$ ed., Tokyo: Newton Press, November 1993, pp. 748-749, pp. 1188-1189.

SUMMARY OF THE INVENTION

As described above, cell behavior can only be assessed in terms of a change between two values by the conventional observation method, and there had yet to be developed an analysis method that can be used when "quantification of change" is needed for time-series changes that occur at such times as when cells collect into a colony, cells degenerate as cell growth is suppressed, and cells separate and disperse.

A determination by microscope observation at regular time intervals requires that the determination be made based on a large number of captured microscopically observed images. In technical fields such as drug development in which cell behavior is observed for each combination of numerous parameters that are varied a small amount at a time, behavior analysis requires significant amounts of time, and the amount of time required has even been indicated as an obstacle to preserving the health and hygiene of the researcher. Furthermore, some drug effects induce death of specific cells, and other effects inhibit growth. Drugs for inhibiting cell growth have generally been evaluated using reagents for cell division assay, and unless the cells are cultured in an environment that supports only a single type of cells, the values obtained include division of other types of cells. In actual practice, however, there are also cells that are controlled by societal interaction with other types of cells, and there is a need for the ability to accurately evaluate these cells.

With the foregoing aspects of the prior art in view, it is an object of the present invention to provide a method for quantitatively assessing the movement state of a cell.

According to a first aspect of the present invention, there is provided an image analysis method for cell observation, comprising: obtaining a first image showing a plurality of cells in an observation region, the first image being captured by an imaging device, and a second image showing the observation region, the second image being captured by the imaging device a predetermined time before the first image is captured; selecting one cell as a cell of interest from the plurality of cells included in the first image; specifying cells on the periphery of the cell of interest as peripheral cells; and calculating movement statistics (e.g., the movement amount $P_{ij}$, movement amount sum $P_i$, and other values in the embodiments) of the peripheral cells with respect to the cell of interest based on an amount of relative movement of the cell of interest and the peripheral cells in the first image and the second image; the image analysis method for cell observation being configured so that a state of interaction of the peripheral cells in relation to the cell of interest can be determined.

According to a second aspect of the present invention, there is provided an image-processing program for cell observation, comprising obtaining a first image showing a plurality of cells in an observation region, the first image being captured by an imaging device, and a second image showing the observation region, the second image being captured by the imaging device a predetermined time before the first image is captured; selecting one cell as a cell of interest from the plurality of cells included in the first image; specifying cells on the periphery of the cell of interest as peripheral cells; calculating movement statistics (e.g., the movement amount $P_{ij}$, movement amount sum $P_i$, and other values in the embodiments) of the peripheral cells with respect to the cell of interest based on an amount of relative movement of the cell of interest and the peripheral cells in the first image and the second image; and outputting the calculated movement statistics of the peripheral cells; the image-processing program for cell observation being configured so that a state of interaction of the peripheral cells in relation to the cell of interest can be determined.

According to a third aspect of the present invention, there is provided an image-processing device for cell observation, comprising an imaging device capturing an image of a cell; an image storage unit storing a first image captured by the imaging device, and a second image captured by the imaging device a predetermined time before the first image is captured; an image analysis unit analyzing a state of interaction between a plurality of the cells positioned in an observation region, based on the first image and the second image; and an output unit outputting analysis data obtained from the image analysis unit; movement statistics (e.g., the movement amount $P_{ij}$, movement amount sum $P_i$, and other values in the embodiments) of peripheral cells with respect to a cell of interest being calculated in the image analysis unit based on an amount of relative movement of the cell of interest and the peripheral cells in the first image and the second image for a single cell of interest selected from a plurality of cells in the observation region of the first image, and peripheral cells positioned on the periphery of the cell of interest; and the movement statistics calculated in the image analysis unit being outputted from the output unit.

According to a fourth aspect of the present invention, there is provided an image analysis method for cell observation, comprising obtaining a first image showing a plurality of cells in an observation region, the first image being captured by an imaging device, and a second image showing the observation region, the second image being captured by the imaging device a predetermined time before the first image is captured; selecting one cell as a cell of interest from the plurality of cells included in the first image; specifying cells on the periphery of the cell of interest as peripheral cells; and calculating velocity statistics of the peripheral cells with respect to the cell of interest based on an amount of relative movement of the cell of interest and the peripheral cells in the first image and the second image; the image analysis method for cell observation being configured so that a state of interaction of the peripheral cells in relation to the cell of interest can be determined.

According to a fifth aspect of the present invention, there is provided an image-processing program for cell observation, comprising obtaining a first image showing a plurality of cells in an observation region, the first image being captured by an imaging device, and a second image showing the observation region, the second image being captured by the imaging device a predetermined time before the first image is captured; selecting one cell as a cell of interest from the plurality of cells included in the first image; specifying cells on the periphery of the cell of interest as peripheral cells; calculating velocity statistics of the peripheral cells with respect to the cell of interest based on an amount of relative movement of the cell of interest and the peripheral cells in the first image and the second image; and outputting the calculated velocity statistics of the peripheral cells; the image-processing program for cell observation being configured so that a state of interaction of the peripheral cells in relation to the cell of interest can be determined.

According to a sixth aspect of the present invention, there is provided an image-processing device for cell observation, comprising an imaging device capturing an image of a cell; an image storage unit storing a first image captured by the imaging device, and a second image captured by the imaging device a predetermined time before the first image is captured; an image analysis unit analyzing a state of interaction between a plurality of the cells positioned in an observation region, based on the first image and the second image; and an output unit outputting analysis data obtained from the image analysis unit; velocity statistics of peripheral cells with respect to a cell of interest being calculated in the image analysis unit based on an amount of relative movement of the cell of interest and the peripheral cells in the first image and the second image for a single cell of interest selected from a plurality of cells in the observation region of the first image, and peripheral cells positioned on the periphery of the cell of interest; and the velocity statistics calculated in the image analysis unit being outputted from the output unit.

Through the image analysis method, image-processing program, and image-processing device for cell observation such as described above, a means can be provided for quantitatively assessing a cell movement state.

BRIEF DESCRIPTION OF THE DRAWINGS

FIG. 8 is a schematic view showing an example of the state of a time-series change of a cell group, and shows a state in which cells that are initially dispersed (1) form a colony (2);
FIG. 14 is a view showing an example of the display image of the cultured cell movement analysis interface displayed on the display panel when the image analysis program is executed.

EXPLANATION OF NUMERALS AND CHARACTERS

Figure 1:
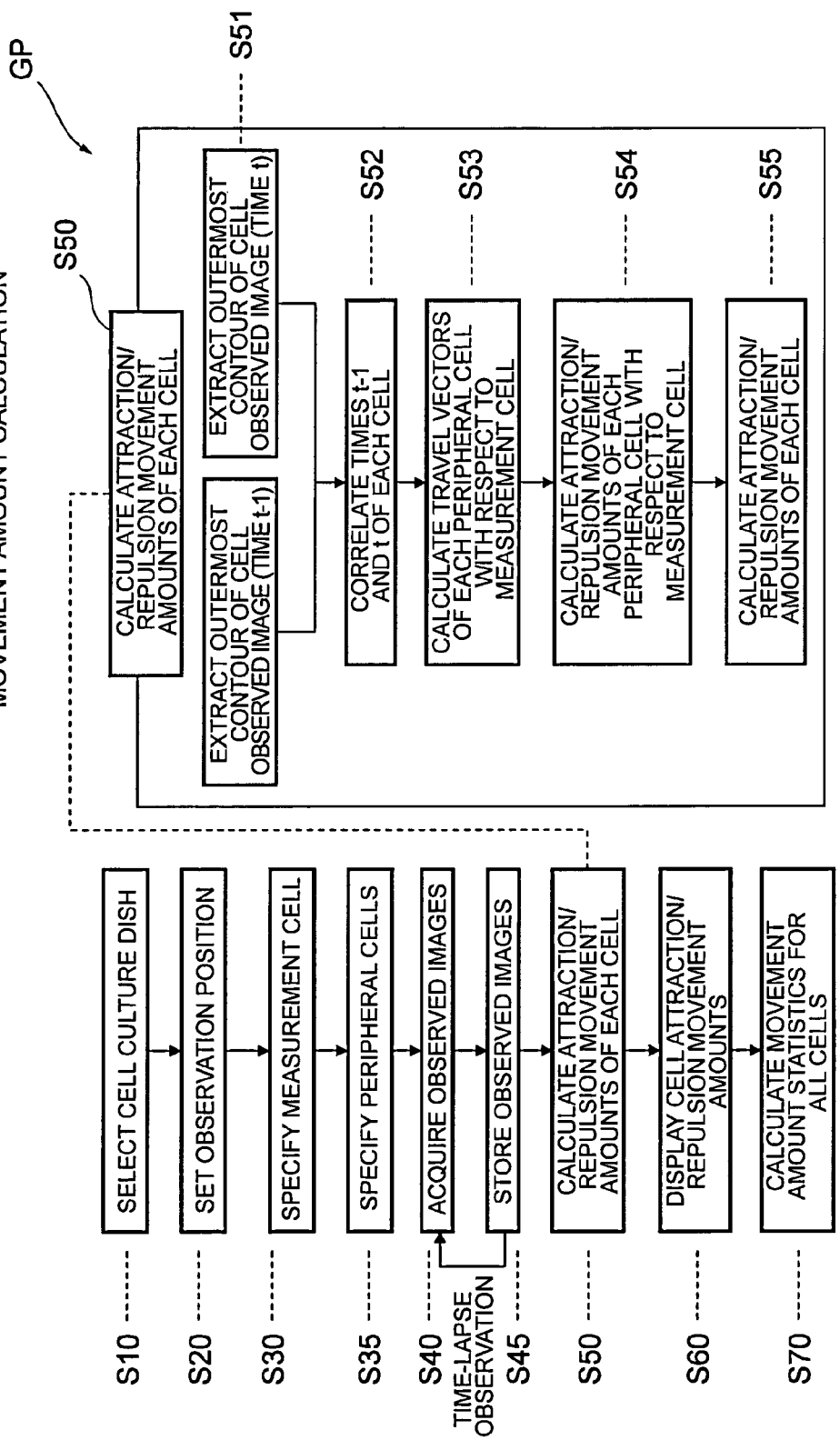
FIG. 1 is a flowchart showing the image-processing program described as an example of the present invention.

BS culture observation system
GP image-processing program
$C_i$ cell of interest
$C_j$ peripheral cell
$C_s$ measurement cell (cell of interest)
54 macro viewing system
54c imaging device
55 microscopy system
55c imaging device
100 image-processing device
110 image storage unit
120 image analysis unit
130 output unit

DESCRIPTION OF THE PREFERRED EMBODIMENTS

A description of the underlying principles of the present embodiment will first be given prior to the description of specific embodiments of the present invention. The present embodiment presents a new feature value for estimating a cell state by quantifying attraction and repulsion between cells as a type of societal interaction.

Figure 2:
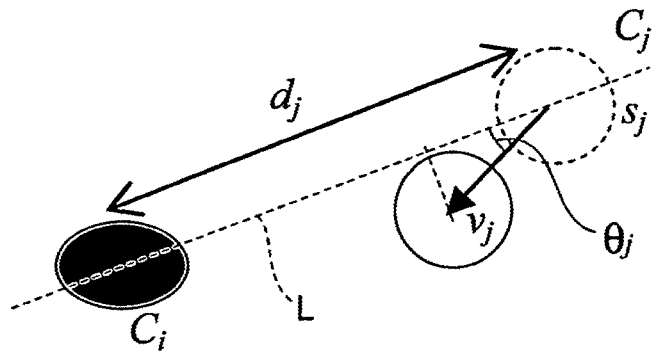
FIG. 2 is a conceptual view showing a movement analysis model for modeling a cell of interest and a peripheral cell.

FIG. 2 is a conceptual view showing a movement analysis model for modeling one cell (cell of interest) $C_i$ and another cell (peripheral cell) $C_j$ that is on the periphery of the cell $C_i$. The area and position (the center of gravity with respect to the cell region, and the position of the cell nucleus) of the cell of interest $C_i$ and the peripheral cell $C_j$ in an image from a certain time t, and the area and position of the same cells in an image at time t-1 prior to time t are detected by image measurement for a time-series image of the cells. The area $s_j$ of the peripheral cell $C_j$ at time t-1, the distance $d_j$ between the cells, the angle $\theta_j$ of the direction of travel from the cell of interest with respect to a line segment L that connects the cells, and the travel distance $v_j$ of the peripheral cell (amount of travel of the peripheral cell $C_j$ relative to the cell of interest $C_i$) from time t-1 to time t are then calculated for the cell of interest $C_i$. The attractive movement amount $P_{ij}$ of the cell of interest $C_i$ toward the peripheral cell $C_j$ at this time is expressed by Equation (1) below.

$$P_{ij} = s_j v_j \cos \theta_j \tag{1}$$

However, for cases in which the distance $d_j$ is significant, a weighting may be applied out of consideration for reliability, such that when the weight function is designated as $W(d_j)$, the attractive movement amount is expressed by Equation (2) below when the distance weight function is considered.

$$P_{ij} = W(d_j) s_j v_j \cos \theta_j \tag{2}$$

The sum of the movement amounts is expressed by Equation (3), where M is the number of peripheral cells.

$$P_i = \sum_{j=1}^{M} W(d_j) s_j v_j \cos \theta_j \tag{3}$$

The statistic $P_{all}$, which is the summation for $i=1, \ldots, N$ in the cell of interest $C_i$ for all the cells in the image (total movement statistic in the claims; referred to hereinafter as "total movement amount"), is calculated by Equation (4) below.

$$P_{all} = \sum_{i=1}^{N} P_i \tag{4}$$

The sign (plus or minus) of the movement amount changes according to the angle $\theta_j$, and attraction and repulsion have opposite signs. Specifically, the total movement amount $P_{all}$ has a large positive value when there is significant attraction between cells, and the total movement amount $P_{all}$ has a large negative value when there is significant repulsion between cells. Consequently, the movement state of the cells can be quantitatively assessed by analyzing the images for time t-1 and time t and calculating the total movement amount of cells in the observation region in the cell viewing process. Besides $1/d_j$ and other weight functions, second-order weighting, Gaussian weighting, and various other weight functions are possible for weighting according to distance $d_j$ $W(d_j)$. The weight function is preferably determined after observing the behavior of cells in relation to each other.

Movement amount is described above, but in the case of movement energy, the sum of the movement energies of M cells on the periphery of a certain cell is expressed by Equation (5), and the total energy $E_{all}$ for all the cells in an image is expressed by Equation (6).

$$E_i = \sum_{j=1}^{M} \frac{1}{2} W(d_j) s_j (v_j \cos \theta_j)^2 \tag{5}$$

$$E_{all} = \sum_{i=1}^{N} E_i \tag{6}$$

Through Equation (6), a value is obtained in which the movement state (activity) of a cell is quantified, the same as in the case of the total movement amount. This value is small when the movement of the plurality of cells in the image is random, but a large value is calculated when there is attraction or repulsion between cells.

Furthermore, attraction and repulsion of cells in the entire image are considered above, but the average values, maximum values, minimum values, histograms, and other values for individual cells expressed by Equations (7) and (8) are also clear indicators that quantitatively express states of cell movement.

$$\bar{P} = \frac{1}{N} \sum_{i=1}^{N} P_i \tag{7}$$

$$\bar{E} = \frac{1}{N} \sum_{i=1}^{N} E_i \tag{8}$$

Consequently, by analyzing a time-series image on the basis of the underlying principle described above, it is possible to observe a time-series change in attractive or repulsive action between cells in the process of cell observation.

An underlying principle is described above whereby cells are observed based on movement amounts according to the movement analysis model shown in FIG. 2, but this underlying principle may also be based on cell attraction/repulsion velocities instead of movement amounts. This underlying principle is described below. For the sake of convenience, the underlying principle of observation based on movement amount will be referred to as the "movement amount principle," and the underlying principle of observation based on attraction/repulsion velocity will be referred to as the "attraction/repulsion principle."

The conceptual view of the movement analysis model shown in FIG. 2 will be referenced in the following description as well. The area and position (the center of gravity with respect to the cell region, and the position of the cell nucleus) of the cell of interest $C_i$ and the peripheral cell $C_j$ in an image from a certain time t, and the area and position of the same cells in an image at time t-1 prior to time t are detected by image measurement for a time-series image of the cells. The distance $d_j$ between the cells at time t-1, the angle $\theta_j$ of the travel direction from the cell of interest with respect to a line segment L that connects the cells, and the travel distance $v_j$ of the peripheral cell (amount of travel of the peripheral cell $C_j$ relative to the cell of interest $C_i$) from time t-1 to time t are then calculated for the cell of interest $C_i$. The attraction/repulsion velocity $V_{ij}$ of the cell of interest $C_i$ toward the peripheral cell $C_j$ at this time is expressed by Equation (9) using the travel distance $v_j$.

$$V_{ij} = v_j \cos \theta_j \tag{9}$$

However, for cases in which the distance $d_j$ is significant, a weighting may be applied out of consideration for reliability, such that when the weight function is designated as $W(d_j)$, the attraction/repulsion velocity is expressed by Equation (10) below when the distance weight function is considered.

$$V_{ij} = W(d_j) v_j \cos \theta_j \qquad (10)$$

The sum $V_i$ of the attraction/repulsion velocities (referred to hereinafter as the "attraction/repulsion amount") is expressed by Equation (11), where M is the number of peripheral cells.

$$V_i = \sum_{j=1}^{M} W(d_j) v_j \cos \theta_j \qquad (11)$$

The statistic, which is the summation of the attraction/repulsion amount $V_i$ for i=1, ..., N in the cell of interest $C_i$ for all the cells in the image (total velocity statistic in the claims; referred to hereinafter as "total attraction/repulsion amount"), is calculated by Equation (12) below.

$$V_{all} = \sum_{i=1}^{N} V_i \qquad (12)$$

The sign (plus or minus) of the attraction/repulsion velocity changes according to the angle $\theta_j$, and attraction and repulsion have opposite signs. Consequently, the total attraction/repulsion amount $V_{all}$ has a large positive value when there is significant attraction between cells, and the total attraction/repulsion amount $V_{all}$ has a large negative value when there is significant repulsion between cells. Consequently, by analyzing the images for time t-1 and time t and calculating the total attraction/repulsion amount for cells in the observation region in the cell viewing process, the movement state of the cells can be quantitatively assessed. Besides $1/d_j$ and other weight functions, second-order weighting, Gaussian weighting, and various other weight functions are possible for weighting $W(d_j)$ according to distance $d_j$. The weight function is preferably determined after the behavior of cells is observed in relation to each other.

Attraction and repulsion of cells in the entire image are considered above, but the average values, maximum values, minimum values, histograms, and other values for individual cells expressed by Equation (13) are also clear indicators that quantitatively express states of cell movement.

$$\overline{V} = \frac{1}{N} \sum_{i=1}^{N} V_i \qquad (13)$$

Consequently, by analyzing a time-series image on the basis of this underlying principle as well (attraction/repulsion principle), it is possible to observe a time-series change in attractive or repulsive action between cells in the process of cell observation.

Figure 3:
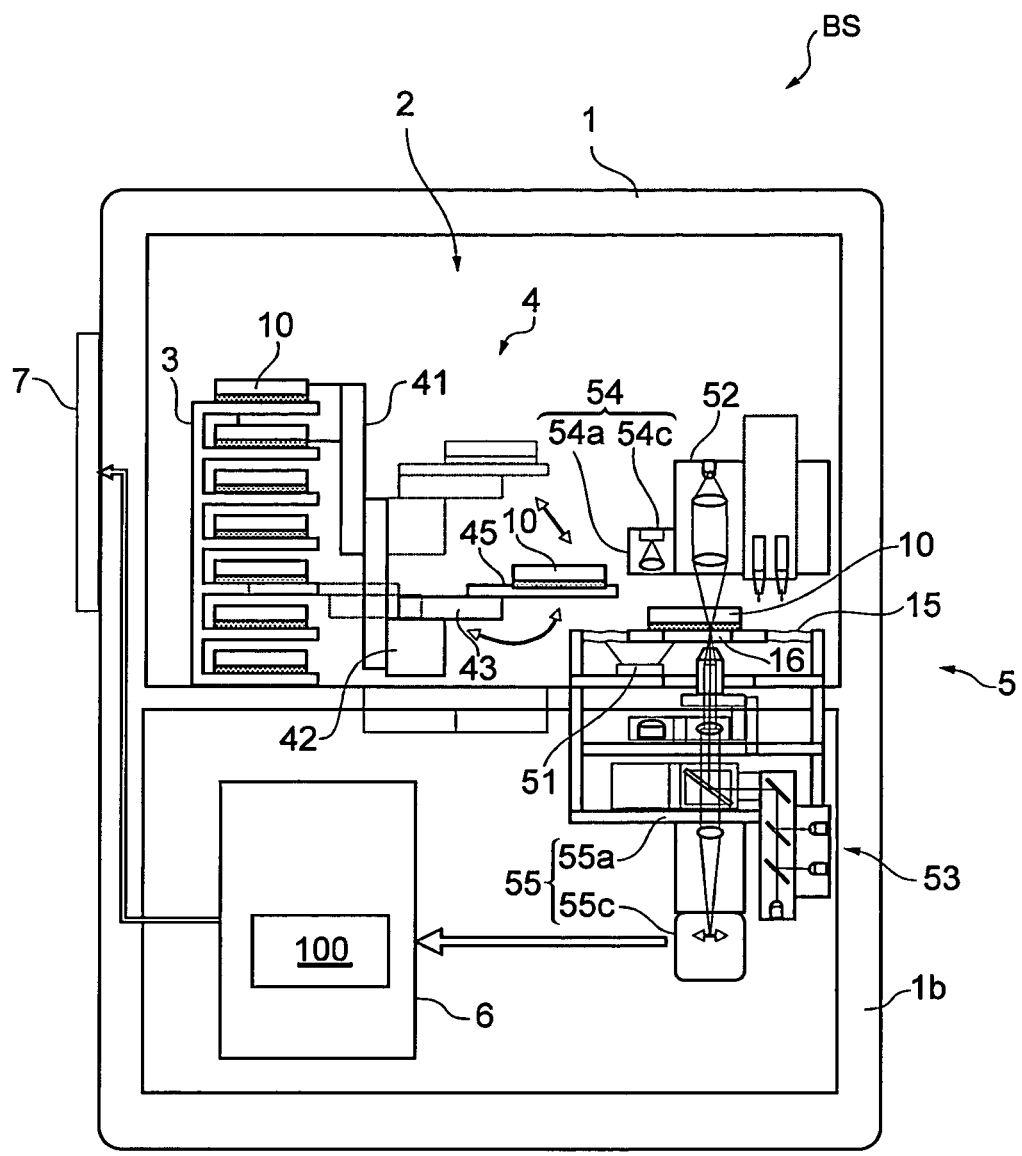
FIG. 3 is a view showing the overall structure of the culture observation system described as an example of an application of the present invention.
Figure 4:
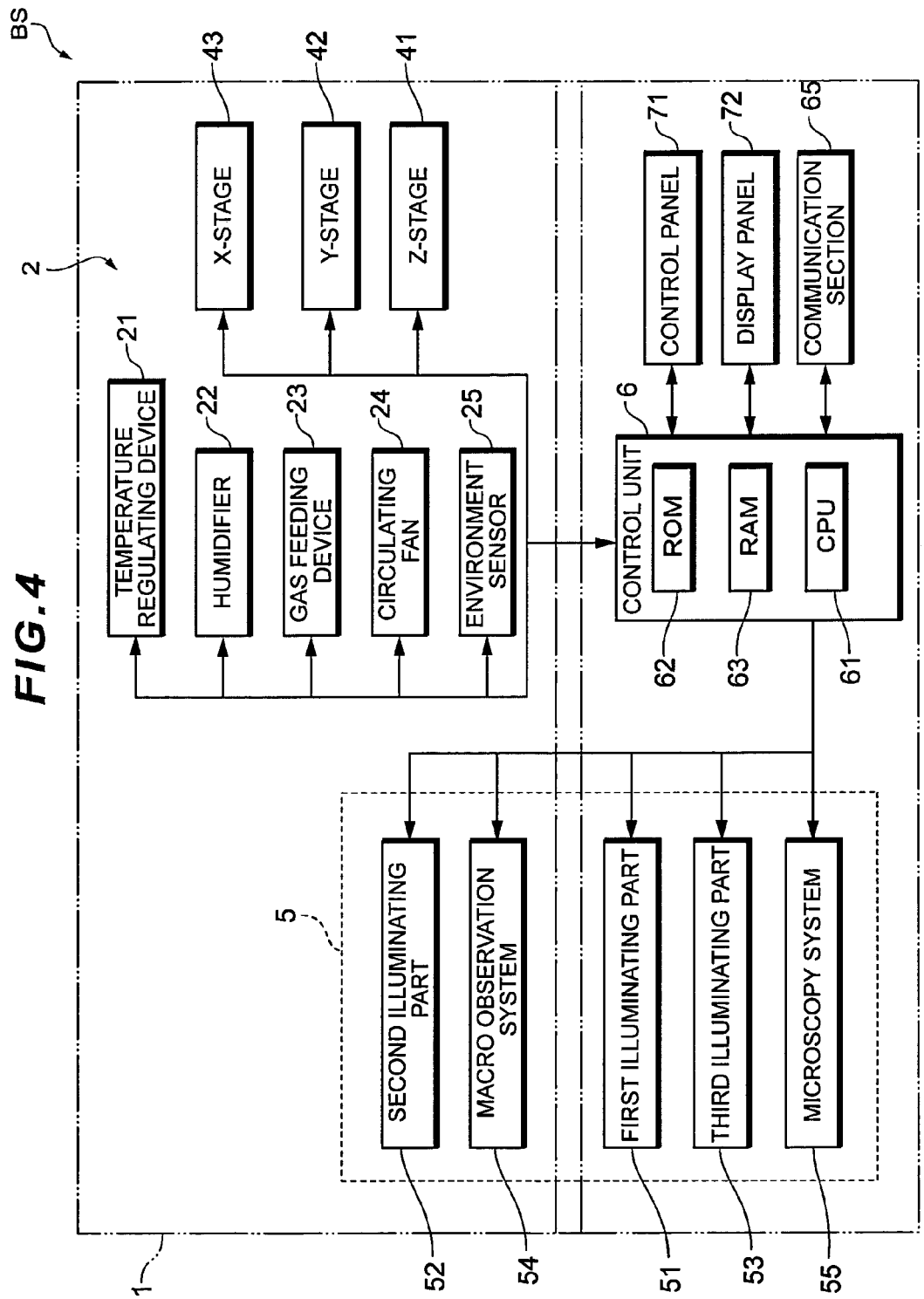
FIG. 4 is a block diagram showing the culture observation system.

Embodiments of the present invention will next be described with reference to the accompanying drawings. FIGS. 3 and 4 are, respectively, a schematic structural view and a block view showing a culture observation system as an example of a system that is an application of the image-processing device for cell observation according to the present embodiment.

The cell culture observation system BS broadly comprises a culture chamber 2 provided to an upper portion of a case 1; a rack-shaped stocker 3 for accommodating and holding a plurality of culture containers 10; an observation unit 5 for observing a sample in a culture container 10; a conveying unit 4 for conveying the culture container 10 between the stocker 3 and the observation unit 5; and a control board 7 having an image display device.

The culture chamber 2 is a chamber in which is formed and maintained a culture environment according to the type, purpose, or other attribute of the cell to be cultured. In order to prevent environmental variation or contamination, the culture chamber 2 is kept in a sealed state after a sample has been introduced thereinto. A temperature regulating device 21 for increasing or decreasing the temperature within the culture chamber; a humidifier 22 for regulating humidity; a gas feeding device 23 for feeding $CO_2$ gas, $N_2$ gas, or another gas; a circulating fan 24 for creating a uniform environment throughout the culture chamber 2; an environment sensor 25 for detecting the temperature, the humidity, and other conditions within the culture chamber 2; and similar devices are provided in association with the culture chamber 2. The operation of each of the devices is regulated by a control unit 6, and a culture environment specified by the temperature, humidity, carbon dioxide concentration, and other conditions in the culture chamber 2 is kept in a state that matches a culture condition set using the control board 7.

As shown in FIG. 3, the stocker 3 is formed to a shape of a rack having a plurality of partitions in the vertical direction and the depth direction running perpendicular to the plane of the diagram. Each rack is assigned a unique address; for example, in an instance where the stocker 3 is divided into columns A through C in the depth direction and rows 1 through 7 in the vertical direction, a rack located at column A, row 5 is assigned an address of A-5.

The culture container 10 may be a flask, a dish, a well plate, or another type of container varying in size and shape, such as round or rectangular. An appropriate culture container 10 may be selected and used in accordance with the type and purpose of the cell to be cultured. A configuration using a dish is shown as an example in the present embodiment. A cell or another sample is injected into the culture container 10 together with a liquid culture medium containing phenol red or another pH indicator. The culture container 10 is given a code number and accommodated in a corresponding specified address in the stocker 3. The culture container 10 is accommodated and stored in each of the racks in a state in which a container holder used for conveyance is attached, the container holder being formed according to the type, format, and similar attributes of the container.

The conveying unit 4 comprises a Z-stage 41, provided within the culture chamber 2 so as to be movable along the vertical direction and moved up or down by a Z-axis driving mechanism; a Y-stage 42 attached to the Z-stage 41 so as to be movable along the depth direction and moved either way by a Y-axis driving mechanism; an X-stage 43 attached to the Y-stage 42 so as to be movable along the lateral direction and moved either way by an X-axis driving mechanism; and other components. A supporting arm 45 for holding and supporting the culture container 10 is provided at a distal end side of the X-stage 43, which moves in the lateral direction relative to the Y-stage. The conveying unit 4 is configured so that the supporting arm 45 has a movement range that allows movement between all of the racks in the stocker 3 and a sample stage 15 of the observation unit 5. Each of the X-axis driving mechanism, the Y-axis driving mechanism, and the Z-axis driving mechanism comprises, for example, a servo motor having a ball screw and an encoder, the operation of each of which driving mechanisms being controlled by the control unit 6.

The observation unit 5 comprises a first illuminating part 51, a second illuminating part 52, a third illuminating part 53, a macro observation system 54 for performing macro observation of the sample, a microscopy system 55 for performing microscopy of the sample, an image-processing device 100, and other components. The sample stage 15 is made from a translucent material, and is provided with a transparent window section 16 located at a region of observation in the microscopy system 55.

The first illuminating part 51 comprises a surface-emitting light source provided on a side towards a lower frame 1*b*, and illuminates the whole of the culture container 10 from below the sample stage 15 in the form of backlight illumination. The second illuminating part 52, provided in the culture chamber 2, has an LED or another light source and an illumination optical system comprising a phase ring, a condenser lens, or a similar component; and illuminates the sample in the culture container from above the sample stage 15 and along an optical axis of the microscopy system 55. The third illuminating part 53 has a plurality of LEDs, mercury lamps, or light sources of another type, each of which used for emitting light of a wavelength that is suitable for epi-illumination observation or fluorescence observation; and an illumination optical system comprising a beam splitter, a fluorescence filter, or another device for superimposing light emitted from each of the light sources onto the optical axis of the microscopy system 55. The third illuminating part 53, provided within the lower frame 1*b* located below the culture chamber 2, illuminates the sample in the culture container from below the sample stage 15 and along an optical axis of the microscopy system 55.

The macro observation system 54, provided in the culture chamber 2 so as to be located above the first illuminating part 51, has an observation optical system 54*a* and a CCD camera or another imaging device 54*c* for capturing an image of the sample formed by the observation optical system. The macro observation system 54 captures an overall observed image (i.e., a macro image) from above the culture container 10 which is backlit by the first illuminating part 51.

The microscopy system 55, provided within the lower frame 1*b*, has an observation optical system 55*a* comprising an objective, a middle zooming lens, a fluorescence filter, and similar components; and a cooled CCD camera or another imaging device 55*c* for capturing an image of the sample formed by the observation optical system 55*a*. Each of the objective and the middle zooming lens is provided in a plural number, and is configured so that a plurality of magnification levels can be set using a revolver, a slider, or another displacement mechanism (not shown in detail). The magnification can be varied between, for example, 2× and 80×, depending on the initially selected lens configuration. The microscopy system 55 captures a microscopically observed picture (i.e., a micro image), obtained by microscopically observing transmitted light illuminated by the second illuminating part 52 and transmitted through the cell, reflected light illuminated by the third illuminating part 53 and reflected by the cell, or fluorescent light emitted by the cell when illumination has been provided by the third illuminating part 53.

The image-processing device 100 performs an analog-to-digital conversion on a signal inputted from the imaging device 54*c* of the macro observation system and the imaging device 55*c* of the microscopy system, performs a variety of types of image-processing, and generates image data for the overall observed image or the microscopically observed image. The image-processing device 100 also performs image analysis on the image data for the observed images, generates a time-lapse image, calculates cell travel, analyzes the cell movement state, or otherwise analyzes the image data. Specifically, the image-processing device 100 is configured by executing an image-processing program stored in a ROM of the control unit 6 described below. The image-processing device 100 will be described in detail further below.

The control unit 6 comprises a CPU 61; a ROM 62, in which a control program for controlling the operation of the cell culture observation system BS, or data for controlling a variety of components, are configured and stored; a RAM 63 for temporarily storing image data and other data; and other devices. In the control unit 6, the devices are connected by a data bus. Connected to an input/output port of the control unit 6 are the temperature regulating device 21, the humidifier 22, the gas feeding device 23, the circulating fan 24, and the environment sensor 25 provided to the culture chamber 2; each of the X-, Y-, and Z-axis driving mechanisms for driving the X, Y, Z stages 43, 42, 41 provided to the conveying unit 4; the first, second, and third illuminating parts 51, 52, 53, the macro observation system 54, and the microscopy system 55 provided to the observation unit 5; a control panel 71 and a display panel 72 provided to the control board 7; and other devices. A detection signal is inputted from each of the devices listed above into the CPU 61, and each of the devices is controlled in accordance with a control program stored in advance in the ROM 62.

The control panel 71, to which is provided a keyboard, a sheet switch, and an input/output device such as a read/write device for reading information from, and writing information to, a magnetic recording medium, an optical disc, or another medium; and the display panel 72, for displaying a variety of operation screens, image data, and other information, are provided to the control board 7. The user configures an observation program (operating condition), selects conditions, and enters an operation command, or other information using the control panel 71 while referring to the display panel 72, and thereby operates, via the CPU 61, the devices provided to the cell culture observation system BS. In other words, in accordance with what is input from the control panel 71, the CPU 61 adjusts the environment in the culture chamber 2; conveys the culture container 10 within the culture chamber 2; observes the sample using the observation unit 5; analyzes obtained image data; displays information on the display panel 72; and performs other operations. The display panel 72 displays numerical values representing environmental conditions in the culture chamber 2, analyzed image data, alerts in the event of a fault, and the like in addition to operation commands, condition selections, and other input screens. The CPU 61 is able to transmit and receive data to and from an externally connected computer or another device via a communication section 65 compliant with wired or wireless telecommunication standards.

The temperature, humidity, or other environmental conditions in the culture chamber 2; an observation schedule for each of the culture containers 10, the type, position, magnification, and other observation conditions associated with the observation unit 5; and other operation conditions for the observation program configured using the control panel 71 are stored in the RAM 63. The code number for each of the culture containers 10 accommodated in the culture chamber 2, the storage address of the culture container 10 in the stocker 3 corresponding to each code number, and other management data for managing the culture container 10; and a variety of data used for the image analysis are also stored in the RAM 63. The RAM 63 is provided with an image data storage region (image storage unit 110 described hereinafter) for storing data relating to captured images obtained using the observation unit 5. Indexing data, containing the code number of the culture container 10, the date and time when the image was captured, and similar information, is stored with the corresponding image data.

In the cell culture observation system BS configured as above, the CPU 61 controls the operation of each of the devices based on the control program stored in the ROM 62 and automatically captures an image of the sample in the culture container 10, according to the conditions set for the observation program as entered using the control board 7. In other words, when operation of the control panel 71 (or remote operation via the communication section 65) starts the observation program, the CPU 61 reads the value of each of the environmental conditions stored in the RAM 63; detects the environmental state in the culture chamber 2 inputted from the environment sensor 25; operates the temperature regulating device 21, the humidifier 22, the gas feeding device 23, the circulating fan 24, and similar devices; and performs feedback control on the temperature, humidity, carbon dioxide concentration, and other culture environment [conditions] in the culture chamber 2.

The CPU 61 reads the observation conditions stored in the RAM 63, operates each of the X-, Y-, and Z-axis driving mechanisms for driving the X, Y, Z stages 43, 42, 41 provided to the conveying unit 4 and conveys the culture container 10 corresponding to the observed object from the stocker 3 to the sample stage 15 in the observation unit 5 according to an observation schedule, and starts observation [of the observed object] by the observation unit 5. For example, in an instance where the observation program has been set for macro observation, the culture container 10 conveyed by the conveying unit 4 from the stocker 3 is positioned on an optical axis of the macro observation system 54 and placed on the sample stage 15, the light source of the first illuminating part 51 is illuminated, and the imaging device 54c is used to capture an overall observation picture from above the backlit culture container 10. A signal sent from the imaging device 54c into the control unit 6 is processed by the image-processing device 100, an overall observed image is generated, and the image data is stored in the RAM 63 together with the indexing data, such as the date and time when the image was captured, and other information.

In an instance where the observation program has been set for microscopy of a sample at a specific location in the culture container 10, the specific location in the culture container 10 conveyed by the conveying unit 4 is positioned on an optical axis of the microscopy system 55 and placed on the sample stage 15, the light source of the second illuminating part 52 or the third illuminating part 53 is illuminated, and the imaging device 55c is used to capture a transmission-illuminated, epi-illuminated, or fluorescence-assisted microscopically observed picture. A signal obtained when an image is captured by the imaging device 55c and sent to the control unit 6 is processed by the image-processing device 100, a microscopically observed image is generated, and the image data is stored in the RAM 63 together with the indexing data, such as the date and time when the image was captured, and other information.

The CPU 61 performs the observation described above on a plurality of samples in culture containers accommodated in the stocker 3, wherein the overall observed picture or the microscopically observed picture is successively captured according to an observation schedule having a time interval of about 30 minutes to 2 hours based on the observation program. According to the present embodiment, the time interval between captured images may be fixed or variable. The image data for the overall observed picture or the microscopically observed picture that has been captured is stored with the code number of the culture container 10 in the image data storage region (image storage unit 110) of the RAM 63. The image data stored in the RAM 63 is read from the RAM 63 according to an image display command inputted from the control panel 71, and an overall observed image or a microscopically observed image at a specified time (i.e., a single image), or a time-lapse image of overall observed pictures or microscopically observed pictures from a specified time region, are displayed on the display panel 72 of the control board 7.

In the culture observation system BS configured as described above, the image-processing device 100 is provided with an image analysis function for analyzing the movement state of the cells in the observation region, in addition to the basic functions described above such as time-lapse image generation. The specific details of the image analysis executed by the image-processing device 100 will be described hereinafter by describing a method for quantitatively calculating the movement state of cells from two time-series images.

(Preprocessing)

Figure 5:
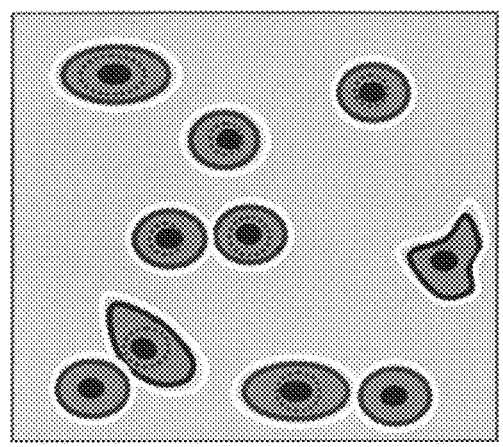
FIG. 5 is a schematic view showing a microscopically observed image of cells captured at time t.
Figure 6:
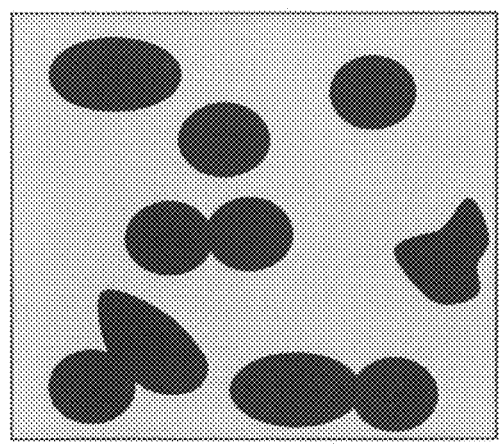
FIG. 6 is a schematic view showing a state in which the microscopically observed image at time t shown in FIG. 5 is segmented.

FIG. 5 is a schematic view showing a microscopically observed image of cells imaged at a certain time t. The regions of each cell in this image are first extracted and segmented. Examples of the method for this extraction include dynamic contour extraction methods such as luminance-based binarization, binarization by dispersion value, and snakes or level set methods. The cell regions thereby segmented as shown in FIG. 6 are labeled, and a method is employed for measuring the labels of the peripheral cells for each cell label.

Figure 7:
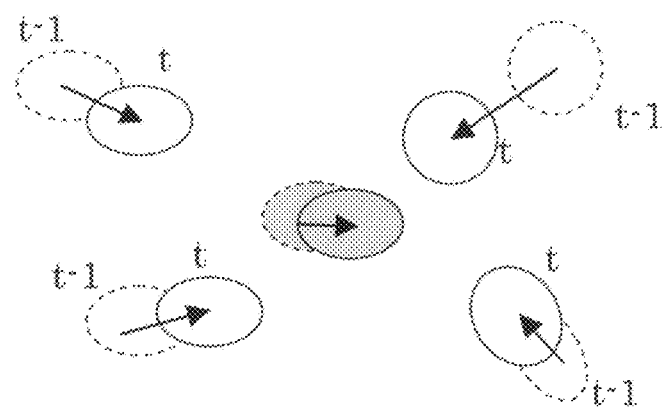
FIG. 7 is a view showing the correlation between cells of the image captured at time t (indicated by solid lines) and cells of an image captured at time t-1 (indicated by dotted lines)

The cells in the image captured at time t (indicated by solid lines), and the cells in the image of time t-1 captured a predetermined time before time t (indicated by dotted lines) are then correlated; i.e., cell tracking is performed, as shown in FIG. 7. The cells that are closest to each other and that have the most similar shape are selected for the cell region labels at time t and time t-1. The travel vectors of each cell from time t-1 to time t are thereby calculated.

(Calculation of Attraction and Repulsion)

An attraction or repulsion movement statistic (which is based on the movement amount principle, and, when based on the attraction/repulsion principle, is referred to as a "velocity statistic") of the cell of interest $C_i$ and a single peripheral cell $C_j$ is calculated for the travel vector of each cell obtained by preprocessing. Typical examples of the movement statistic are the movement amount or movement energy (which is based on the movement amount principle, and, when based on the attraction/repulsion principle, is referred to as the "attraction/repulsion velocity" or "attraction/repulsion amount") of the peripheral cell $C_j$ with respect to the cell of interest $C_i$. As shown in FIG. 2, the characteristics from time t-1 to time t of the one peripheral cell $C_j$ with respect to the cell of interest $C_i$ include the characteristics shown below.

Cell area $s_j$: area within contour of peripheral cell $C_j$

Travel distance $v_j$: amount of travel of peripheral cell $C_j$ relative to the cell of interest $C_i$ Distance $d_j$: distance between cell of interest $C_i$ and peripheral cell $C_j$ Angle $\theta_j$: the angle of the travel direction with respect to line segment L that connects the cells In a case in which the cells both contribute an ionic substance, and an attraction or repulsion is effected according to the concentration thereof, the resulting energy is inversely proportional to the distance $d_j$ between the cells, and the weight function $W(d_j)$ in this case is expressed by Equation (14). The weight function is expressed by Equation (15) when the area is relevant.

$$W(d_j) = \frac{1}{d_j} \quad (14)$$

$$W(d_j) = \frac{1}{d_j^2} \quad (15)$$

Equation (16) can be used as the weight function when the weighting can be set within a certain range. In Equation (16), D is a user-specified range of interaction between cells.

$$W(d_j) = \begin{cases} 1 & (d_i \leq D) \\ 0 & (d_j > D) \end{cases} \quad (16)$$

In more probabilistic terms, the weight function may be defined as a probability density function using the normal distribution (where σ is the standard deviation) defined by Equation (17).

$$W(d_j) = \frac{1}{\sqrt{2\pi\sigma^2}} \exp\left(-\frac{d_j^2}{2\sigma^2}\right) \quad (17)$$

When based on the movement amount principle, the movement amount $P_{ij}$ imparted to the single peripheral cell $C_j$ by the cell of interest $C_i$ at this time is expressed by Equation (18).

$$P_{ij} = W(d_j)s_j v_j \cos\theta_j \quad (18)$$

When this operation is applied to all of the peripheral cells (numbering M), the sum $P_i$ of the attraction/repulsion movement amounts of the cell of interest $C_i$ are as expressed by Equation (19).

$$P_i = \sum_{j=1}^{M} W(d_j)s_j v_j \cos\theta_j \quad (19)$$

The sign (plus or minus) of the movement amount sum $P_i$ changes according to the angle $\theta_j$, and attraction and repulsion have opposite signs. It is therefore possible to distinguish whether each cell of interest is being attracted or repulsed, as well as the magnitude of the attraction or repulsion. The total movement amount $P_{all}$ for all the cells in the image is calculated according to Equation (20) by substituting the cell of interest $C_i$ for i=1 through N.

$$P_{all} = \sum_{i=1}^{N} P_i \quad (20)$$

As described above, the total movement amount $P_{all}$ has a large positive value when there is significant attraction between cells, and has a large negative value when there is significant repulsion between cells. Consequently, by analyzing the two images for time t-1 and time t and calculating the total movement amount of cells in the observation region, it is possible to quantitatively assess the movement state of the cells, as well as to distinguish between attraction and repulsion in the cell viewing process.

Figure 9:
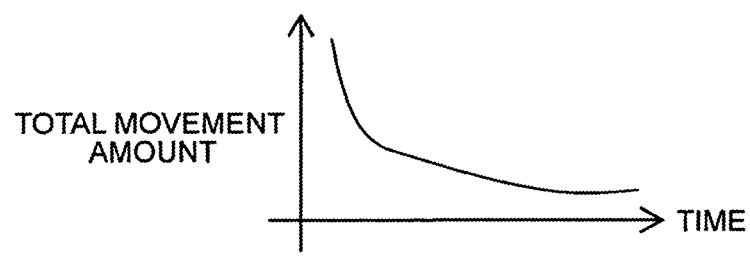
FIG. 9 is a graph showing the change in attraction and repulsion when a cell group forms a colony, where the value of the total movement statistic calculated at each predetermined time is plotted on a graph with time indicated on the horizontal axis.

For time-series data in which a state change occurs such as the one shown in FIG. 8 with the references (1) and (2), a change graph in which the change in attraction is visualized is obtained by displaying in a time series the values of the total movement amounts calculated at each predetermined time, and plotting the values on a graph in which time is indicated on the horizontal axis, as shown in FIG. 9. The transformation from initially separate cells to an aggregated colony is thereby shown quantitatively, and the change in the cell group can be quantitatively and easily assessed.

The time-series changes in the average values for individual cells, maximum values, minimum values, histograms, and other statistics as expressed by Equations (21) through (23) are also of significant interest as indicators of the cell movement state. Attraction and repulsion may also be observed separately by treating only positive values (attraction) or only negative values (repulsion).

$$\bar{P} = \frac{1}{N}\sum_{i=1}^{N} P_i \quad (21)$$

$$P_{max} = \max_i P_i \quad (22)$$

$$P_{min} = \min_i P_i \quad (23)$$

When movement energy is used as the movement statistic, the sum $E_i$ of the movement energies of the M peripheral cells on the periphery of the cell of interest is determined by Equation (24), and the total energy $E_{all}$ for all the cells in the image is the value calculated by Equation (25), which quantitatively indicates the movement state (activity) of the cells.

$$E_i = \sum_{j=1}^{M} \frac{1}{2} W(d_j)s_j(v_j\cos\theta_j)^2 \quad (24)$$

$$E_{all} = \sum_{i=1}^{N} E_i \quad (25)$$

This value is near zero when the movement of the plurality of cells in the image is random, but a large value is calculated when there is attraction or repulsion between cells. Consequently, the movement state (activity state) of the cells can also be quantitatively assessed when movement energy is used as the movement statistic, by analyzing the two images for time t-1 and time t and calculating the total movement energy of the cells in the observation region in the cell observation process. The same applies for average values for individual cells, and the maximum values, minimum values, and histograms.

When based on the attraction/repulsion principle, following the definition of the probability density function of Equation (17), the attraction/repulsion velocity $V_{ij}$ imparted to the single peripheral cell $C_j$ by the cell of interest $C_i$ at this time is expressed by Equation (26).

$$V_{ij} = W(d_j)v_j \cos\theta_j \quad (26)$$

Applying this equation to all the peripheral cells (numbering M), the attraction/repulsion amount $V_i$ exerted by the cell of interest $C_i$ is expressed by Equation (27).

$$V_i = \sum_{j=1}^{M} W(d_j) v_j \cos\theta_j \qquad (27)$$

The total attraction/repulsion amount for all the cells in the image is calculated by Equation (28), which is the summation when the cell of interest $C_i$ is substituted for i=1 through N.

$$V_{all} = \sum_{i=1}^{N} V_i \qquad (28)$$

As described above, the total attraction/repulsion amount $V_{all}$ has a large positive value when there is significant attraction between cells, and a large negative value when there is significant repulsion between cells. Consequently, by analyzing the two images for time t-1 and time t and calculating the total attraction/repulsion amount $V_{all}$ of cells in the observation region, it is possible to quantitatively assess the movement state of the cells, as well as to distinguish between attraction and repulsion in the cell viewing process.

For time-series data in which a state change occurs such as the one shown in FIG. 8 with the references (1) and (2), a change graph in which the change in attraction is visualized is obtained by displaying in a time series the values of the total attraction/repulsion amounts calculated at each predetermined time, and plotting the values on a graph in which time is indicated on the horizontal axis, as shown in FIG. 9. The transformation from initially separate cells to an aggregated colony is thereby shown quantitatively, and the change in the cell group can be quantitatively and easily assessed.

The time-series changes in the average values for individual cells, maximum values, minimum values, histograms, and other statistics as expressed by Equations (29) through (31) are also of significant interest as indicators of the cell movement state. Attraction and repulsion may also be observed separately by treating only positive values (attraction) or only negative values (repulsion).

$$\overline{V} = \frac{1}{N} \sum_{i=1}^{N} V_i \qquad (29)$$

$$V_{max} = \max_i V_i \qquad (30)$$

$$V_{min} = \min_i V_i \qquad (31)$$

Examples are described below of applications for the technique described above of calculating movement statistics (which is based on the movement amount principle, and, when based on the attraction/repulsion principle, is referred to as a "velocity statistic") by image analysis and viewing interaction between cells.

(A: Specifying a Measurement Cell)

Figure 10:
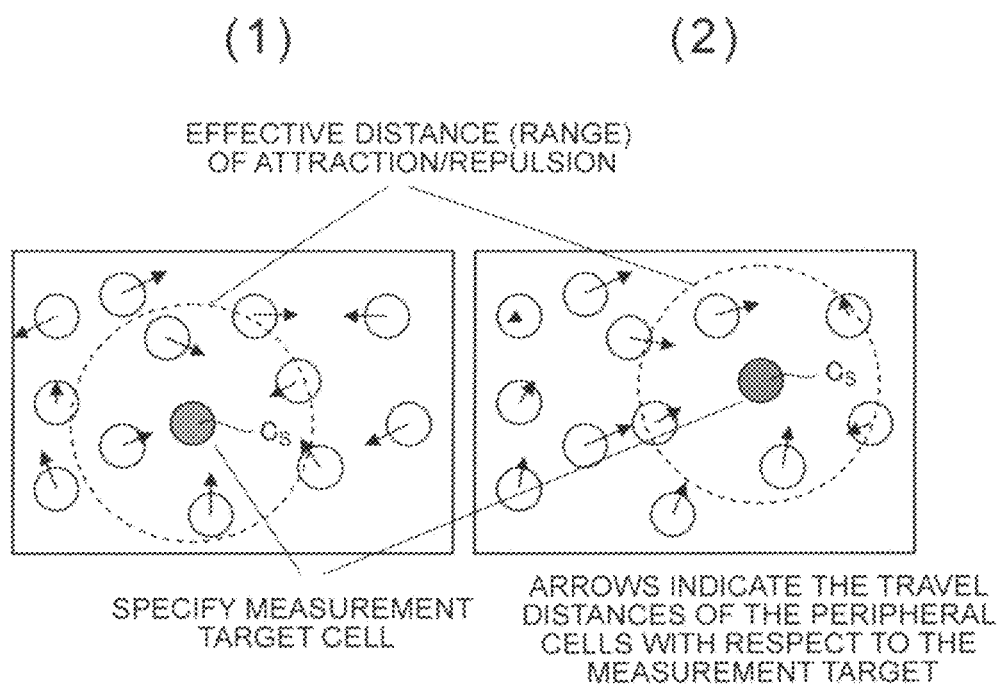
FIG. 10 is a schematic view showing the manner in which the measurement cell to be measured is specified.
Figure 11:
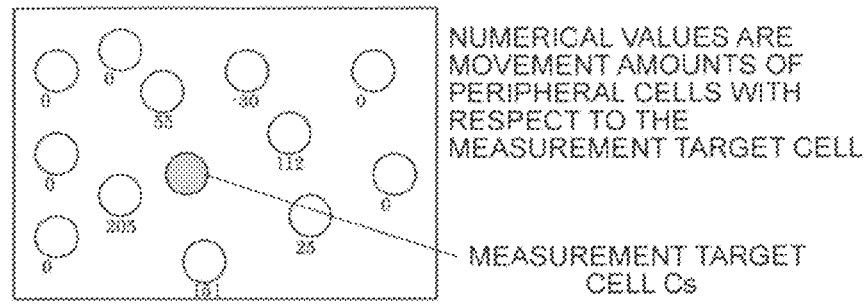
FIG. 11 is a view showing an example of the configuration of the screen for displaying the movement amount (relative movement amount) of the peripheral cells with respect to the measurement cell.

An observer specifies one or a plurality of cells to be measured and calculates the total movement amount/energy of attraction or repulsion with respect to the specified measurement cell (when based on the movement amount principle; a "calculation of total attraction/repulsion velocity" is performed when the basis is the attraction/repulsion principle). For example, as shown in FIG. 10 with the references (1) and (2), a specific cell is designated as a measurement cell $C_s$ from among numerous cells included in the image, an effective distance (range) of attraction or repulsion is set, and calculations are made of the total movement amount/energy of attraction or repulsion with respect to the specified measurement cell $C_s$ (when based on the movement amount principle; an "attraction/repulsion velocity" is calculated when the basis is the attraction/repulsion principle). The movement amounts of the peripheral cells with respect to the single cell $C_s$ specified as the measurement target (when based on the movement amount principle; "attraction/repulsion velocities" are displayed when the basis is the attraction/repulsion principle) are displayed as shown in FIG. 11. Each of the movement states with respect to the measurement cell $C_s$, the cell exerting the most attraction or repulsion, and other characteristics can thereby be known.

(B: Statistical Calculation and Time-Series Change in Attraction/Repulsion Movement Amounts or Velocities)

Figure 12:
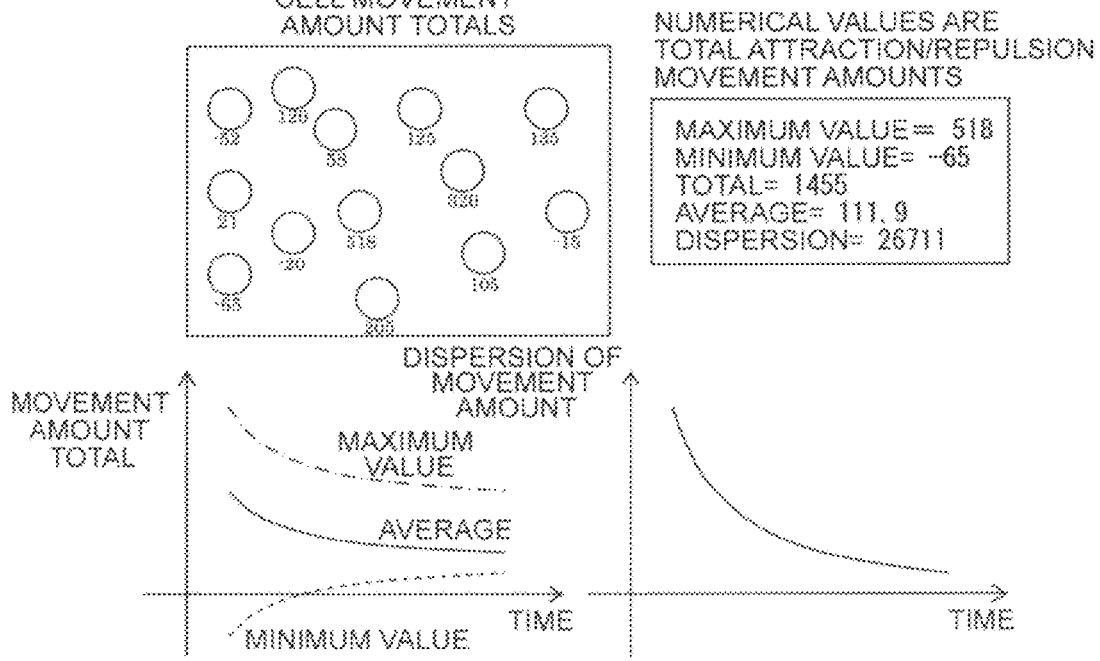
FIG. 12 is a view showing an example of the configuration of the screen for displaying the sum of the movement amounts.

As shown in FIG. 12, when the measurement cell $C_s$ specified in part A is substituted with the other cells in order, a calculation is made of the movement amounts of each cell (when based on the movement amount principle; "attraction/repulsion velocities" are calculated when the basis is the attraction/repulsion principle), and the sum of the calculated movement amounts (or attraction/repulsion velocities) is calculated for each cell and displayed for each cell, it is possible to ascertain the cell exerting the most influence by looking at the maximum value in the field of view. The overall state can be ascertained by displaying the average value, maximum value, minimum value, and dispersion, which are statistics for the total movement amount (or total velocity) of each cell. Plotting the time-series data on a graph along a time axis enables the change to be easily assessed in the time region. The velocity, size (area), shape (including roundness, complexity, and other aspects), and other time-series variations of the measurement cell $C_s$ specified in part A can also be displayed, whereby a detailed assessment of the movement state of the cell can be made.

Figure 13:
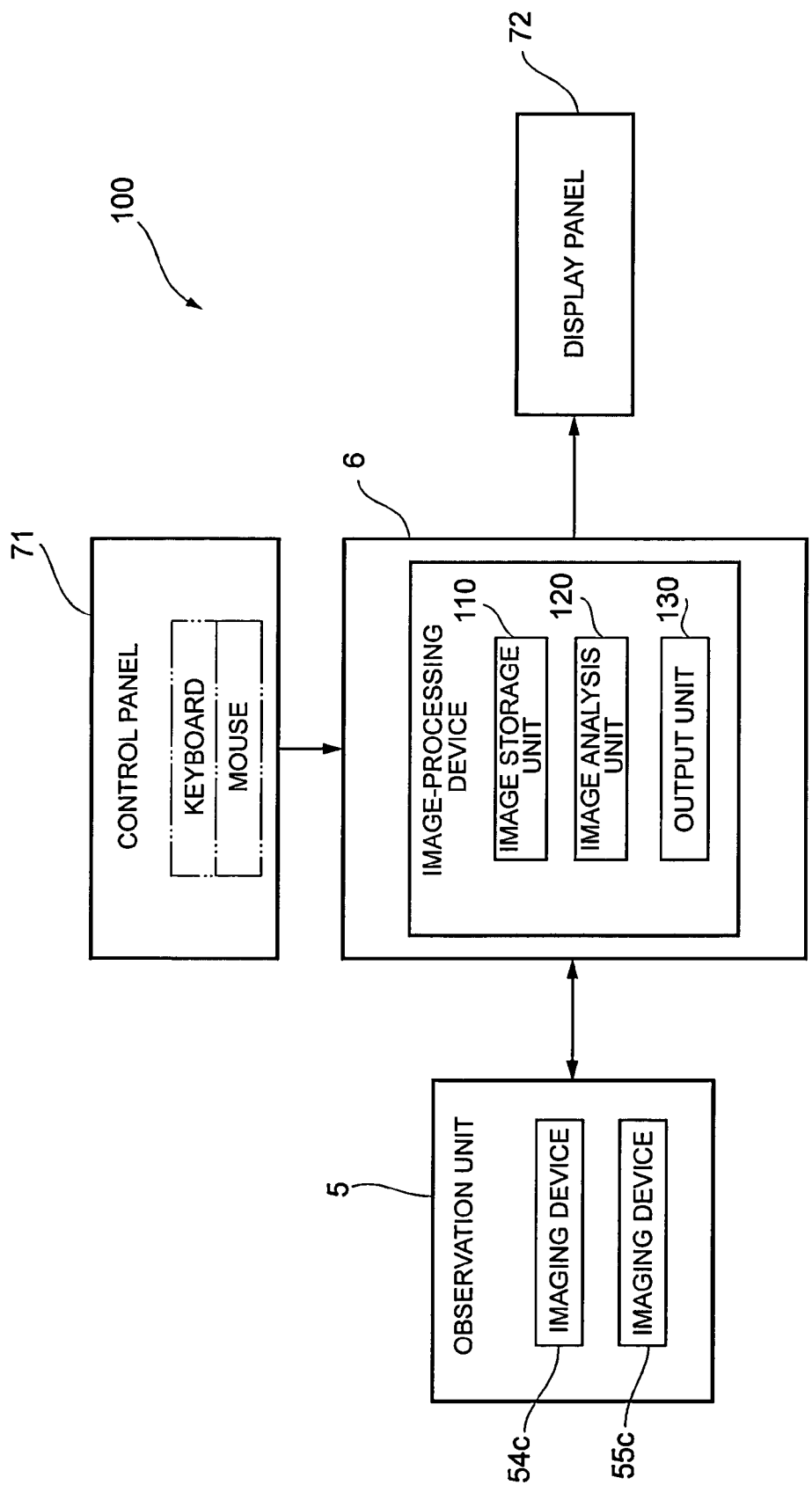
FIG. 13 is a block diagram showing the overall structure of the image-processing device.

A specific application of the image analysis executed in the image-processing device 100 will next be described using an example in which a microscopically observed image (phase contrast image) of a living cell is analyzed. FIG. 13 is a block diagram showing the overall structure of the image analysis unit for performing image analysis of the movement state of a cell in the image-processing device 100.

The image-processing device 100 comprises an image storage unit 110 for storing a first image captured by an imaging device (54c, 55c), and a second image captured at a time t-1 a predetermined time before the first image has been captured; an image analysis unit 120 for analyzing a state of interaction (state of attraction or repulsion) between a plurality of the cells positioned in an observation region, on the basis of the first image and the second image; and an output unit 130 for outputting analysis data from the image analysis unit 120. The image-processing device 100 is configured so that attraction or repulsion movement amounts between cells are calculated in the image analysis unit 120 on the basis of the relative positions and relative travel distances of the cell of interest and the peripheral cells in the first image and the second image, the movement amounts are added together to calculate the total movement amount (or attraction/repulsion amount) of the cell of interest, the movement amounts (or attraction/repulsion amounts) calculated by sequentially substituting the cell of interest are added together to calculate the total movement amounts (or total attraction/repulsion amounts) of all of the plurality of cells, and the results are outputted from the output unit 130 for display on, e.g., a display panel 72.

In the image-processing device 100, an image-processing program stored in advance in the ROM 62 is read by a CPU 61, and processing based on the image-processing program is executed by the CPU 61.

Not only can the image analysis process of the present embodiment be executed for time-series images previously captured at a predetermined time interval based on an observation program and stored in the image storage unit 110, but the movement state of cells can also be analyzed and monitored in real time at the time of observation. This real-time image analysis processing will therefore be described in the present example with reference to the flowchart of FIG. 1 showing the image-processing program GP, and the display screen shown in FIG. 14 for the cultured cell movement analysis interface that is displayed on the display panel 72.

In this interface, a "dish selection" box 721 is displayed on the display panel 72, code numbers are displayed for culture containers accommodated in the stocker 3, and in step S10, a culture container 10 is selected for observation. FIG. 14 shows a state in which the cell culture dish (culture container) having the code number Cell-0002 is selected by the cursor provided to the control panel 71.

When the observation target is selected in step S10, the CPU 61 operates the drive mechanisms of the shafts of the conveyance unit 4, and the culture container 10 corresponding to the observation target is conveyed from the stocker 3 to the observation unit 5. An overall observed image obtained using the macro observation system 54 or a microscopically observed image obtained using the microscopy system 55 is captured by the imaging device (54c, 55c), and is displayed in the "viewing position" box 722.

In step S20, the viewing position is set to determine which region is the observation region. FIG. 14 shows a state in which the observer uses a mouse or other instrument provided to the control panel 71 to specify a shaded region at the center right. At this time, segmentation processing is immediately performed in the image analysis unit 120 for the image of the designated observation region, and an image in which the cell contours are superimposed on the phase contrast image, or a schematic view (segmentation image) according to cell contours is displayed in the "observed image" box 723. At this time, a "movement analysis options" box 724 is displayed that includes a "measurement cell specification" area 724a and a "peripheral cell specification" area 724b.

In step S30, the observer uses the mouse to select a measurement target cell for which the observer wishes to know the movement amount (or attraction/repulsion velocity) from the schematic view displayed in the "observed image" box 723, and presses the confirmation button in the "measurement cell specification" area 724a to confirm the measurement cell $C_s$. In the next step S35, manual selection of the peripheral cell $C_j$ or specification thereof by distance (radius) from the measurement cell $C_s$ is selected using the selection button provided to the "peripheral cell specification" area 724b. In the case of manual selection, peripheral cells $C_j$ are individually selected using the mouse and confirmed by pressing the confirmation button. In the case of selection by radius, the radius value is inputted numerically (using pixels, microns, or other units) or by mouse.

Using these initial settings, observed images are acquired (step S40) according to an observation schedule at predetermined times set in the observation program, the observed images are stored (step S45), and time-lapse observation is performed. Cell images of the measurement cell $C_s$ and peripheral cells $C_j$ in the observation region set in steps S30 and S35 are segmented and tracked in the image analysis unit 120 at each predetermined time set in the observation schedule, and the movement amounts (or attraction/repulsion velocities) of the cells are calculated in step S50.

The details of the calculation (step S50) of cell movement amounts (or attraction/repulsion velocities) are as previously described, and the flow thereof (steps S51 through S55) is also briefly summarized in the form of a flowchart on the right-hand side of FIG. 1. Specifically, in the calculation of the movement amount (or attraction/repulsion velocity) of each cell that is performed in the image analysis unit 120, the outermost contours of the cells are extracted as shown in FIG. 6 for the observed image (first image) of time t and the observed image (second image) of time t-1 captured a predetermined time before the first image (segmentation processing: step S51), the measurement cell $C_s$ is correlated with the peripheral cells $C_j$ as shown in FIG. 7 between the two images (step S52), the travel vectors of the peripheral cells $C_j$ with respect to the measurement cell $C_s$ are calculated according to the abovementioned correlation (step S53), and the movement amount (or attraction/repulsion velocity) of each peripheral cell $C_j$ with respect to the measurement cell $C_s$ is calculated based on the abovementioned travel vectors by the method described using the travel model of FIG. 2 (step S54). The attraction/repulsion movement amount (or attraction/repulsion velocity) of each cell is calculated; i.e., the sum $P_i$ (or attraction/repulsion amount $V_i$) of the movement amounts in relation to the cell of interest $C_i$ is calculated for M peripheral cells, the sum of the movement amounts (attraction/repulsion amounts) of the cells when the cell of interest is substituted is calculated, and the results of calculating the attraction/repulsion movement amount (attraction/repulsion amount) of each cell are outputted from the output unit 130 (step S55).

In step S60, the movement amounts (or attraction/repulsion velocities) or the peripheral cells $C_j$ such as shown in FIG. 11, or the total movement amounts (attraction/repulsion amount) relating to each cell such as shown in FIG. 12 are displayed in real time on the display screen of the "observed image" box 723 at each observation, and the values of the calculated cell movement amounts (or attraction/repulsion velocities) are stored in the RAM 63. Substituting the measurement cell $C_s$ as the cell of interest $C_i$ for i=1 through N, the movement amount total (total movement amount) $P_{all}$ (or total attraction/repulsion amount $V_{all}$) for all the cells included in the observation region is calculated in step S70, the results are stored in the RAM 63, and the movement amount totals (attraction/repulsion amounts) for all the cells can be displayed as shown in FIG. 12. The interface is configured so that the selection button provided to the "observed image" box 723 can be used to select whether to display movement amounts (attraction/repulsion velocities) of the peripheral cells as shown in FIG. 11, or to display movement amount totals (attraction/repulsion amounts) for all the cells as shown in FIG. 12.

During time-lapse observation, a real-time display appears as a graph in a "time-series change graph" box 725. This graph displays the maximum values, minimum values, average values, and other changes over time of the cell movement amounts (or attraction/repulsion amounts), as previously described with reference to FIG. 12. Changes in the velocity, area, and shape (roundness, complexity, and other aspects) of the measurement cell $C_s$ over time can also be displayed, and the display can be switched by selecting the items to be displayed in the time-series change graph. An output terminal is furthermore provided to the output unit 130 and connected to a communication section 65, and the calculation results can be exported to an externally connected computer or the like via the communication section 65.

Consequently, through such image analysis means (image analysis method, image-processing program, and image-processing device), the moment-to-moment movement state of cells under observation can be displayed in real time by specific numerical values or graphs during time-lapse observation, and the state of cell movement can be rapidly and quantitatively assessed.

In the above example, a configuration is described in which the measurement cell $C_s$ and the peripheral cells $C_j$ are specified at the start of time-lapse observation, image analysis is executed in parallel during the course of time-lapse observation, and the results of analysis are displayed in real time. However, the image analysis of the present invention can also be implemented for time-series images stored in the image storage unit 110 when a time-lapse observation for a certain period of time is executed (during execution), or after a time-lapse observation is completed. The flow of image analysis for such a case will be briefly described below with reference to FIGS. 1 and 14.

First, in step S10, a culture container (e.g., the previously described cell culture dish having the code number Cell-0002) having the code number corresponding to the observation target is selected from the list of culture containers displayed in the "dish selection" box 721. Time-series images corresponding to the selected observation target are already stored in the image storage unit 110 (i.e., steps S40 and S45 in the image-processing program shown in FIG. 1 were executed prior to step S10). Therefore, when the observation target is selected in step S10, the observed image (overall observed image or microscopically observed image) for time t of the selected culture container is read from the image storage unit 110 and displayed in the "viewing position" box 722. The image of a particular time during the observation period can be selected; e.g., the start of observation (second data) can be selected, or an intermediate or end time point in the observation period can be selected.

In step S20, the observation region is set to determine which region of the image displayed in the "observation position" box to observe. The image of the designated observation region is immediately subjected to segmentation processing in the image analysis unit 120, and an image in which the cell contours are superimposed on the phase contrast image, or a schematic view according to cell contours is displayed in the "observed image" box. Segmentation processing is performed for the image for time t and the image for time t-1 captured a predetermined time before the first image is captured, and the schematic view can be displayed for time t only, or a time-series display can be provided for both times.

The cell corresponding to the measurement target is then selected on the schematic view displayed in the "observed image" box 723 in step S30, and the confirmation button in the "measurement cell specification" area 724a is pressed to confirm selection of the measurement cell $C_s$. The peripheral cells $C_j$ are specified manually or by distance (radius) from the measurement cell $C_s$ in step S35, and the confirmation button is pressed for confirmation. The selected settings thereof are the same as previously described.

When the settings for the measurement cell $C_s$ and the peripheral cell $C_j$ are confirmed in steps S30 and S35, the image analysis unit 120 first calculates the cell movement amounts and movement amount totals (attraction/repulsion velocities and attraction/repulsion amounts) of step S50, and the total movement amounts (total attraction/repulsion amounts) for all the cells of step S70 for the images from time t and time t-1 read from the image storage unit 110, and stores the results in the RAM 63. The observed images already captured according to a predetermined observation schedule and stored in the image storage unit 110 (step S40, step S45) are read by sequentially shifting time t, the image of the observation region set in step S20 is cut from each read image and subjected to segmentation and tracking, and the calculations of steps S50 and S70 are executed in order and the results stored in the RAM 63.

The movement amounts (attraction/repulsion velocities) of the peripheral cells shown in FIG. 11, or the movement amount totals or total movement amounts (attraction/repulsion amounts or total attraction/repulsion amounts) of all the cells shown in FIG. 12 are then displayed according to the selection made using the selection button provided to the "observed image" box 723. This display may show the results calculated for a specific time that is arbitrarily selected. When a time-lapse observation is under way, the change in the movement amount (attraction/repulsion amount) (maximum value, minimum value, average value, and other values) up to the present time is displayed as a graph in the "time-series change graph" box 725, and when observation has already been completed, the change in the movement amount (attraction/repulsion amount) from the start of observation to the end thereof is displayed.

As described above, through the image-processing program GP and the image analysis method and image-processing device 100 configured to execute this image-processing program according to the present invention, from cell observed images captured at predetermined times are used to calculate total movement statistics (total attraction/repulsion amounts) for all the cells at the time images are captured. Means can therefore be provided for rapidly and quantitatively assessing the state of cell movement.

As described above, societal interactions are important to cell growth. In the present invention, by calculating attraction and repulsion, it is possible to quantitatively evaluate the processes by which other cells are attracted, scaffolding is formed, or other types of cells are invaded. In other words, the present invention can be used to screen reagents for suppressing normal growth in isolation from other cells, or to screen reagents for suppressing invasion of other cells.

The embodiments can be implemented in computing hardware (computing apparatus) and/or software, such as (in a non-limiting example) any computer that can store, retrieve, process and/or output data and/or communicate with other computers. The results produced can be displayed on a display of the computing hardware. A program/software implementing the embodiments may be recorded on computer-readable media comprising computer-readable recording media. The program/software implementing the embodiments may also be transmitted over transmission communication media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW. An example of communication media includes a carrier-wave signal. The media described above may be non-transitory media.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. An image analysis method for cell observation, comprising:
obtaining a first image showing a plurality of cells in an observation region, the first image being captured by an imaging device, and a second image showing the observation region, the second image being captured by the imaging device a predetermined time before the first image is captured;
selecting one cell as a cell of interest from the plurality of cells included in the first image;
specifying cells on the periphery of the cell of interest as peripheral cells; and
calculating movement statistics of the peripheral cells with respect to the cell of interest based on an amount of relative movement of the cell of interest and the peripheral cells in the first image and the second image; and
adding together the movement statistics obtained by sequentially substituting the selected cell of interest with other cells positioned in the observation region, and calculating a total movement statistic for all of the cells in the observation region,
the image analysis method for cell observation being configured so that a state of interaction of the peripheral cells in relation to the cell of interest can be determined and that a state of interaction between cells in the observation region can be evaluated based on the total movement statistic.

2. The image analysis method for cell observation according to claim 1, wherein the movement statistics are amounts of movement of the peripheral cells with respect to the cell of interest.

3. The image analysis method for cell observation according to claim 1, wherein the movement statistics are movement energies of the peripheral cells with respect to the cell of interest.

4. The image analysis method for cell observation according to claim 1, wherein a weight corresponding to the distance between the cell of interest and the peripheral cells is assigned to the movement statistics.

5. The image analysis method for cell observation according to claim 1, wherein the state of interaction is a state of attraction or repulsion.

6. An image-processing program stored on a non-transitory medium for cell observation, comprising:
obtaining a first image showing a plurality of cells in an observation region, the first image being captured by an imaging device, and a second image showing the observation region, the second image being captured by the imaging device a predetermined time before the first image is captured;
selecting one cell as a cell of interest from the plurality of cells included in the first image;
specifying cells on the periphery of the cell of interest as peripheral cells;
calculating movement statistics of the peripheral cells with respect to the cell of interest based on an amount of relative movement of the cell of interest and the peripheral cells in the first image and the second image;
outputting the calculated movement statistics of the peripheral cells;
adding together the movement statistics obtained by sequentially substituting the selected cell of interest with other cells positioned in the observation region, and calculating a total movement statistic for all of the cells in the observation region; and
outputting the calculated total movement statistic,
the image-processing program for cell observation being configured so that a state of interaction of the peripheral cells in relation to the cell of interest can be determined and that a state of interaction between cells in the observation region can be evaluated based on the total movement statistic.

7. The image-processing program for cell observation according to claim 6, wherein the movement statistics are amounts of movement of the peripheral cells with respect to the cell of interest.

8. The image-processing program for cell observation according to claim 6, wherein the movement statistics are movement energies of the peripheral cells with respect to the cell of interest.

9. The image-processing program for cell observation according to claim 6, wherein a weight corresponding to the distance between the cell of interest and the peripheral cells is assigned to the movement statistics.

10. The image-processing program for cell observation according to claim 6, wherein the state of interaction is a state of attraction or repulsion.

11. The image-processing program for cell observation according to claim 6, further comprising computing the total movement statistic for each of the predetermined times for three or more images captured by the imaging device at each of the predetermined times, the captured images being in sequence as the first image, and displaying the total movement statistics in a time series in an image display device,
the image-processing program for cell observation being configured so that a temporal change in the total movement statistics can be assessed.

12. An image-processing device for cell observation, comprising:
an imaging device capturing an image of a cell;
an image storage unit storing a first image captured by the imaging device, and a second image captured by the imaging device a predetermined time before the first image is captured;
an image analysis unit analyzing a state of interaction between a plurality of the cells positioned in an observation region based on the first image and the second image; and
an output unit outputting analysis data obtained from the image analysis unit,
movement statistics of peripheral cells with respect to a cell of interest being calculated in the image analysis unit based on an amount of relative movement of the cell of interest and the peripheral cells in the first image and the second image for a single cell of interest selected from a plurality of cells in the observation region of the first image, and peripheral cells positioned on the periphery of the cell of interest,
the movement statistics obtained by sequentially substituting the selected cell of interest with other cells positioned in the observation region are added together, and a total movement statistic for all of the cells in the observation region is calculated,
the movement statistics and the total movement statistic calculated in the image analysis unit being outputted from the output unit.

13. The image-processing device for cell observation according to claim 12, wherein the movement statistics are amounts of movement of the peripheral cells with respect to the cell of interest.

14. The image-processing device for cell observation according to claim 12, wherein the movement statistics are movement energies of the peripheral cells with respect to the cell of interest.

15. The image-processing device for cell observation according to claim 12, wherein a weight corresponding to the distance between the cell of interest and the peripheral cells is assigned to the movement statistics.

16. The image-processing device for cell observation according to claim 12, wherein the state of interaction is a state of attraction or repulsion.

17. The image-processing device for cell observation according to claim 12, further comprising an image display device for displaying an image,
the total movement statistic being computed in the image analysis unit for each of the predetermined times for three or more images captured by the imaging device at each of the predetermined times, the captured images being in sequence as the first image, and
the image-processing device for cell observation being configured so that the total movement statistics for each of the predetermined times are outputted from the output unit to the image display device and displayed in a time series in the image display device, and a temporal change in the total movement statistics can be visually assessed.

18. An image analysis method for cell observation, comprising:
obtaining a first image showing a plurality of cells in an observation region, the first image being captured by an imaging device, and a second image showing the observation region, the second image being captured by the imaging device a predetermined time before the first image is captured;
selecting one cell as a cell of interest from the plurality of cells included in the first image;
specifying cells on the periphery of the cell of interest as peripheral cells;
calculating velocity statistics of the peripheral cells with respect to the cell of interest based on an amount of relative movement of the cell of interest and the peripheral cells in the first image and the second image; and
adding together the velocity statistics obtained by sequentially substituting the selected cell of interest with other cells positioned in the observation region, and calculating a total velocity statistic for all of the cells in the observation region,
the image analysis method for cell observation being configured so that a state of interaction of the peripheral cells in relation to the cell of interest can be determined and that a state of interaction between cells in the observation region can be evaluated based on the total velocity statistic.

19. The image analysis method for cell observation according to claim 18, wherein a weight corresponding to the distance between the cell of interest and the peripheral cells is assigned to the velocity statistics.

20. The image analysis method for cell observation according to claim 18, wherein the state of interaction is a state of attraction or repulsion.

21. An image-processing program stored on a non-transitory medium for cell observation, comprising:
obtaining a first image showing a plurality of cells in an observation region, the first image being captured by an imaging device, and a second image showing the observation region, the second image being captured by the imaging device a predetermined time before the first image is captured;
selecting one cell as a cell of interest from the plurality of cells included in the first image;
specifying cells on the periphery of the cell of interest as peripheral cells;
calculating velocity statistics of the peripheral cells with respect to the cell of interest based on an amount of relative movement of the cell of interest and the peripheral cells in the first image and the second image;
outputting the calculated velocity statistics of the peripheral cells;
adding together the velocity statistics obtained by sequentially substituting the selected cell of interest with other cells positioned in the observation region, and calculating a total velocity statistic for all of the cells in the observation region; and
outputting the calculated total velocity statistic,
the image-processing program for cell observation being configured so that a state of interaction of the peripheral cells in relation to the cell of interest can be determined and that a state of interaction between cells in the observation region can be evaluated based on the total velocity statistic.

22. The image-processing program for cell observation according to claim 21, wherein a weight corresponding to the distance between the cell of interest and the peripheral cells is assigned to the velocity statistics.

23. The image-processing program for cell observation according to claim 21, wherein the state of interaction is a state of attraction or repulsion.

24. The image-processing program for cell observation according to claim 21, further comprising computing the total velocity statistic for each of the predetermined times for three or more images captured by the imaging device at each of the predetermined times, the captured images being in sequence as the first image, and displaying the total velocity statistics in a time series on an image display device,
the image-processing program for cell observation being configured so that a temporal change in the total velocity statistics can be assessed.

25. An image-processing device for cell observation, comprising:
an imaging device capturing an image of a cell;
an image storage unit storing a first image captured by the imaging device, and a second image captured by the imaging device a predetermined time before the first image is captured;
an image analysis unit analyzing a state of interaction between a plurality of the cells positioned in an observation region based on the first image and the second image; and
an output unit outputting analysis data obtained from the image analysis unit,
velocity statistics of peripheral cells with respect to a cell of interest being calculated in the image analysis unit on the basis of the amount of relative movement of the cell of interest and the peripheral cells in the first image and the second image for a single cell of interest selected from a plurality of cells in the observation region of the first image, and peripheral cells positioned on the periphery of the cell of interest,
the velocity statistics obtained by sequentially substituting the selected cell of interest with other cells positioned in the observation region are added together, and a total velocity statistic for all of the cells in the observation region is calculated, and the velocity statistics and the total velocity statistic calculated in the image analysis unit being outputted from the output unit.

26. The image-processing device for cell observation according to claim 25, wherein a weight corresponding to the distance between the cell of interest and the peripheral cells is assigned to the velocity statistics.

27. The image-processing device for cell observation according to claim 25, wherein the state of interaction is a state of attraction or repulsion.

28. The image-processing device for cell observation according to claim 25, further comprising an image display device for displaying an image, the total velocity statistic being computed in the image analysis unit for each of the predetermined times for three or more images captured by the imaging device at each of the predetermined times, the captured images being in sequence as the first image, and the image-processing device for cell observation being configured so that the total velocity statistics for each of the predetermined times are outputted from the output unit to the image display device and displayed in a time series in the image display device, and a temporal change in the total velocity statistics can be visually assessed.

* * * * *